United States Patent
Masuda et al.

(10) Patent No.: US 7,680,242 B2
(45) Date of Patent: Mar. 16, 2010

(54) X-RAY EXAMINATION METHOD AND X-RAY EXAMINATION APPARATUS

(75) Inventors: Masayuki Masuda, Nishinomiya (JP); Tsuyoshi Matsunami, Kyotanabe (JP); Haruyuki Koizumi, Kyoto (JP); Noriyuki Kato, Nara (JP)

(73) Assignee: Omron Corporation, Kyoto-shi (JP)

( * ) Notice: Subject to any disclaimer, the term of this patent is extended or adjusted under 35 U.S.C. 154(b) by 0 days.

(21) Appl. No.: 12/047,803

(22) Filed: Mar. 13, 2008

(65) Prior Publication Data
US 2008/0226023 A1    Sep. 18, 2008

(30) Foreign Application Priority Data
Mar. 13, 2007  (JP)  ............................ P2007-063871

(51) Int. Cl.
*G01N 23/00*    (2006.01)
(52) U.S. Cl. ............................. 378/19; 378/13; 378/58; 378/62; 378/137
(58) Field of Classification Search ...................... 378/4, 378/9–13, 19, 51, 54, 55, 57, 58, 62, 91, 378/92, 93, 137
See application file for complete search history.

(56) References Cited

U.S. PATENT DOCUMENTS 7,106,830 B2 * 9/2006 Rosner .................... 378/146
7,406,152 B2 * 7/2008 Teramoto et al. ............. 378/58

FOREIGN PATENT DOCUMENTS

| JP | 06-100451 | 12/1994 |
|---|---|---|
| JP | 2000-046760 | 2/2000 |
| JP | 2003-344316 | 12/2003 |
| JP | 2006-162335 | 6/2006 |

* cited by examiner

*Primary Examiner*—Jurie Yun
(74) *Attorney, Agent, or Firm*—Foley & Lardner LLP

(57) ABSTRACT

An X-ray examination apparatus includes a scanning X-ray source for outputting X-rays, a sensor base which is attached with a plurality of X-ray sensors and which rotates about a rotation axis, and an image acquiring control mechanism for controlling rotation angle of the sensor base and acquisition of image data from the X-ray sensors. With respect to each X-ray sensor, the scanning X-ray source moves the X-ray focal position of the X-ray source to each starting position of the X-ray emission set so that the X-ray transmits through a predetermined examination area of an examination target and enters each X-ray sensor, and emits the X-rays. The image control acquiring control mechanism acquires image data detected by the X-ray sensors, and a calculation unit reconstructs an image of the examination area based on the image data.

9 Claims, 14 Drawing Sheets

| Examination area | Sensor name | Sensor inclination angle | Sensor imaging angle | Focal position | Irradiation angle | Sensor arrangement angle |
|---|---|---|---|---|---|---|
| S0 | A | αA | βA | A0 | θA | γA |
|  | B | αB | βB | B0 | θB | γB |
|  | ... | ... | ... | ... | ... | ... |
|  | N | αN | βN | N0 | θN | γN |
| S0 (Rotation) | A | αA | β'A | A'0 | θA | γA |
|  | B | αB | β'B | B'0 | θB | γB |
|  | ... | ... | ... | ... | ... | ... |
|  | N | αN | β'N | N'0 | θN | γN |
| ... |  |  |  |  |  |  |

200  202  204  206  208  210  212

X-RAY EXAMINATION METHOD AND X-RAY EXAMINATION APPARATUS

This application claims priority from Japanese Patent Application P2007-063871, filed on Mar. 13, 2007. The entire content of the aforementioned application is incorporated herein by reference.

BACKGROUND OF THE INVENTION

1. Field of the Invention

The present invention relates to an X-ray examination method and an X-ray examination apparatus. In particular, the present invention relates to a photographing method for examining an object using X-ray irradiation, which is a technique applicable to an X-ray examination method and an X-ray examination apparatus.

2. Description of the Related Art

Recently, with high integration of an LSI (Large-Scale Integration) by submicron microfabrication technique, functions which were conventionally divided into a plurality of packages can now be integrated into one LSI. Since the increase in the number of pins that arise as a result of incorporating the functions necessary for one package cannot be responded with the conventional QFP (Quad Flat Package) and PGA (Pin Grid Array), LSIs of BGA (Ball Grid Array) and CSP (Chip Size Package) package, in particular, are recently being used. The BGA package is used where ultraminiaturization is necessary such as a mobile phone even if the required number of pins is not large.

The BGA and CSP package of LSI greatly contributes to ultraminiaturization, but has a feature that the solder portion and the like cannot be seen from the outer appearance after assembly. When inspecting a printed board and the like mounted with the BGA or CSP package, the quality determination is performed by analyzing a transmitted image obtained by irradiating an object to be examined with an X-ray.

For instance, Japanese Laid-Open Patent Publication No. 2000-46760 discloses an X-ray sectional examination apparatus capable of obtaining a clear X-ray image by using an X-ray planar sensor to detect the transmitted X-ray.

Japanese Laid-Open Patent Publication No. 2003-344316 discloses a method of reconstructing an image in an inclined three-dimensional X-ray CT by appropriately selecting the irradiation angle of the X-ray.

Japanese Laid-Open Patent Publication No. 2006-162335 discloses an X-ray examination apparatus capable of performing a two-dimensional examination based on an X-ray image acquired with parallel X-ray detection means and a three-dimensional examination based on an X-ray image acquired with inclined X-ray detection means to perform both the examinations at a high speed.

Japanese Laid-Open Patent Publication No. 06-100451 discloses an automatic laminographic system for creating a cross-sectional image of a connecting part of an electronic component, automatically identifying a fault of the connecting part and finding the position by the analysis system, and determining process characteristics of the connecting part.

However, in the X-ray photographing technique relating to the conventional X-ray examination described above, time is required for imaging and 3D (reconstruction) calculation if the area of an examination area that can be reconstructed is increased. For instance, in order to examine a printed board and the like as described above, images of a plurality of specific portions will suffice in most cases, instead of an image of the entire examination target. In this case, when portions to be examined in the target of examination are arranged in a scattered state, it is not efficient to prepare an X-ray detector having an area (or volume) that encompasses the entire region as the target of examination from the viewpoint of enlargement in device, increase in calculation load, and the like.

An imaging system or an examination target workpiece needs to be moved to change the examination area, whereby movable portions increase. Thus, problems in cost, maintenance, and reliability arise.

Furthermore, when changing the examination area in a case where the area of the examination target is large (e.g., a glass substrate), it is sometimes difficult to move the workpiece side in the X-Y direction or rotate the same over 360 degrees.

SUMMARY OF THE INVENTION

In view of solving the above problems, it is an object of the present invention to provide an X-ray examination apparatus capable of selectively examining at a high speed a predetermined area of an examination target object, and an X-ray examination method using such an X-ray photographing method.

It is another object of the present invention to provide an X-ray examination apparatus that has reduced movable portions, that is of low cost, and that excels in maintenance and reliability, and an X-ray examination method using such an X-ray photographing method.

It is still another object of the present invention to provide an X-ray examination apparatus capable of examining an examination target object having a large area without moving the examination target object, and an X-ray examination method using such an X-ray photographing method.

According to one aspect of the present invention, there is provided an X-ray examination method using an X-ray examination apparatus including a light receiving part for detecting an X-ray transmitted through an object by X-ray irradiation with a plurality of detection surfaces, the method including the steps of: specifying an examining portion of the object; generating the X-ray by moving, with respect to the plurality of detection surfaces, an X-ray focal position of an X-ray source to each starting position of the X-ray emission set such that the X-ray transmits through the examining portion and enters each of the detection surfaces; detecting an intensity distribution of the X-ray transmitted through the examining portion at each of the detection surfaces; and reconstructing image data of the examining portion based on data of the detected intensity distribution.

Preferably, the step of generating the X-ray includes: specifying a plurality of detection surfaces for detecting the X-ray; setting each starting position on a target surface which is a continuous surface of the X-ray source such that the examining portion is on a straight line from each of the plurality of detection surfaces to the starting position; and generating the X-ray by changing an irradiation position to apply an electron beam of the X-ray source to each starting position and moving the X-ray focal position.

Preferably, the step of setting each starting position includes the step of determining an intersection of a straight line connecting the detection surface with the examining portion and the target surface as the starting position.

Preferably, the step of generating the X-ray includes the step of changing the irradiation position by deflecting the electron beam.

Preferably, the step of specifying the examining portion includes the step of specifying an examining portion to be examined for this time to a position moved along a direction from the target surface towards the object from the examined examining portion.

According to another aspect of the present invention, there is provided an X-ray examination apparatus including a light receiving part for detecting an X-ray transmitted through an object by X-ray irradiation with a plurality of detection surfaces, the X-ray examination apparatus including: a detection unit including the plurality of detection surfaces; and an output controller for controlling an output process of the X-ray; wherein the output controller includes: a specifying part for specifying an examining portion of the object; a starting point setting part for setting, with respect to the plurality of detection surfaces, each starting position of the X-ray emission such that the X-ray transmits through the examining portion of the object and enters each of the detection surfaces; an X-ray output part for moving an X-ray focal position of an X-ray source to each starting position and generating the X-ray; and a reconstruction part for reconstructing image data of the examining portion based on data of an intensity distribution of the X-ray transmitted through the examining portion detected at the plurality of detection surfaces.

Preferably, the X-ray output part includes a part for deflecting an electron beam of the X-ray source and changing an irradiation position of applying the electron beam to move the X-ray focal position.

Preferably, the detection unit includes: a rotatable base arranged with the plurality of detection surfaces on a circumference having a predetermined axis as a center; and a rotating part for rotating the rotatable base about the axis.

Preferably, the plurality of detection surfaces is arranged on a circumference having an axis perpendicular to the object as a center.

Preferably, the plurality of detection surfaces is arranged on a plurality of circumferences having different radiuses with an axis perpendicular to the object as a center.

Preferably, the detection unit includes a part for freely moving each detection surface in a radial direction of a circle having the perpendicular axis as the center.

Preferably, the detection unit includes a detection surface controller for controlling an inclination angle formed by an axis perpendicular to the object and each detection surface.

According to the X-ray examination method and the X-ray examination apparatus of the present invention, a predetermined examination area of an examination target object can be selectively examined at a high speed.

DETAILED DESCRIPTION OF THE PREFERRED EMBODIMENTS

Figure 1:
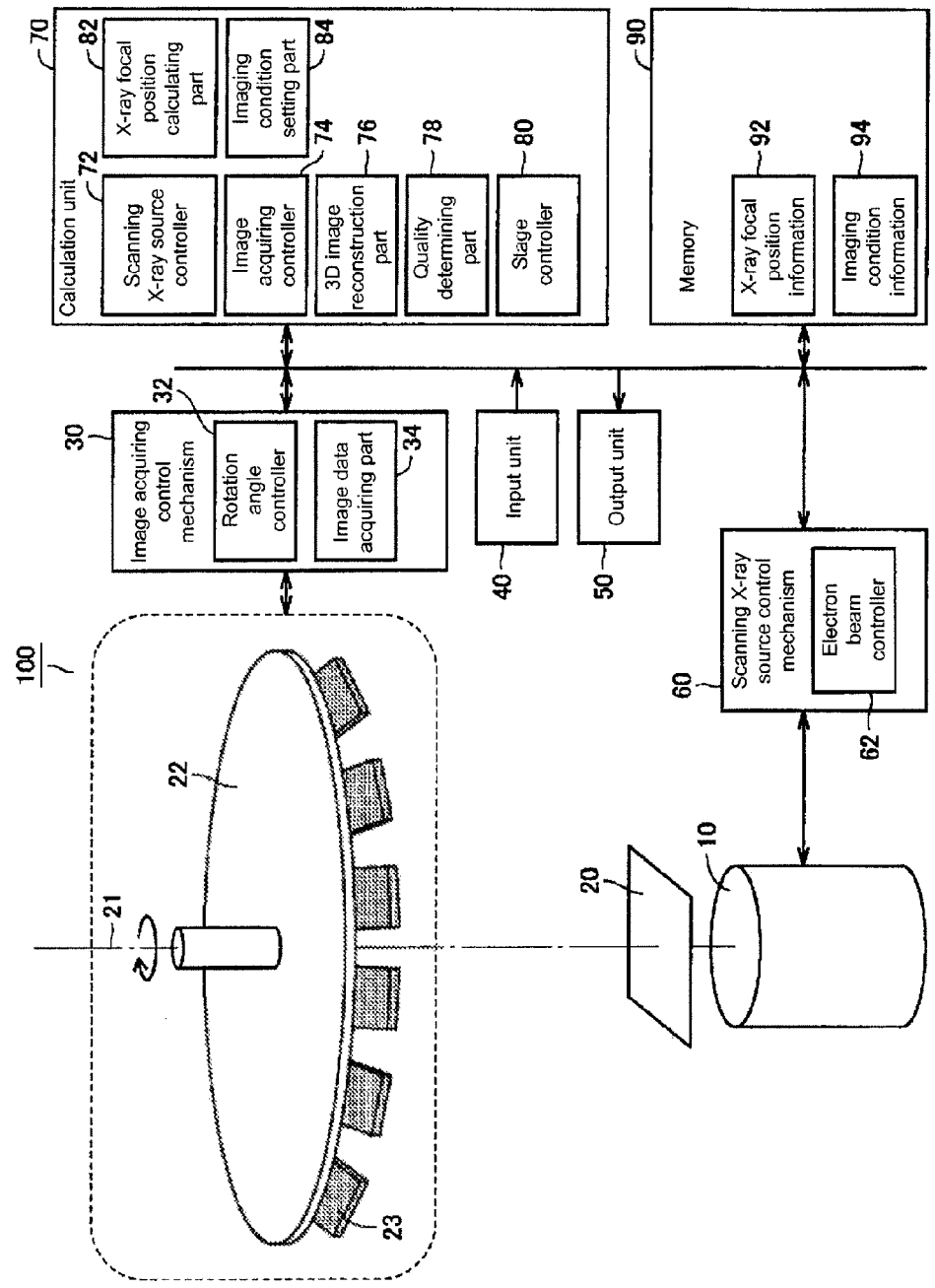
FIG. 1 shows a schematic block diagram of an X-ray examination apparatus 100 according to the present invention.

Preferred embodiments of the present invention will be described with reference to the drawings. In the following description, the same reference numerals are given for the same components. The names and functions thereof are also the same. Therefore, detailed description thereon will not be repeated.

(1. Configuration of the Present Invention)

FIG. 1 shows a schematic block diagram of an X-ray examination apparatus 100 according to the present invention.

The X-ray examination apparatus 100 according to the present invention will be described with reference to FIG. 1. It should be noted that the configuration, dimensions, shape, and other relative arrangement described below are not intended to exclusively limit the scope of the present invention unless specifically stated.

The X-ray examination apparatus 100 includes a scanning X-ray source 10 for outputting X-rays, and a sensor base 22 attached with a plurality of X-ray sensors 23 and being a rotatable base that rotates about a rotation axis 21. An examination target 20 is arranged between the scanning X-ray source 10 and the sensor base 22. The X-ray examination apparatus 100 also includes an image acquiring control mechanism 30 for controlling acquisition of a rotation angle about the rotation axis of the sensor base 22 and image data from the X-ray sensors 23, an input unit 40 for accepting instruction input and the like from a user, and an output unit 50 for outputting a measurement result and the like to the outside. The X-ray examination apparatus 100 further includes a scanning X-ray source control mechanism 60, a calculation unit 70, and a memory 90. In such a configuration, the calculation unit 70 executes a program (not shown) stored in the memory 90 to control each unit and performs a predetermined calculation process.

The scanning X-ray source 10 is controlled by the scanning X-ray source control mechanism 60 and irradiates the examination target 20 with X-rays.

Figure 2:
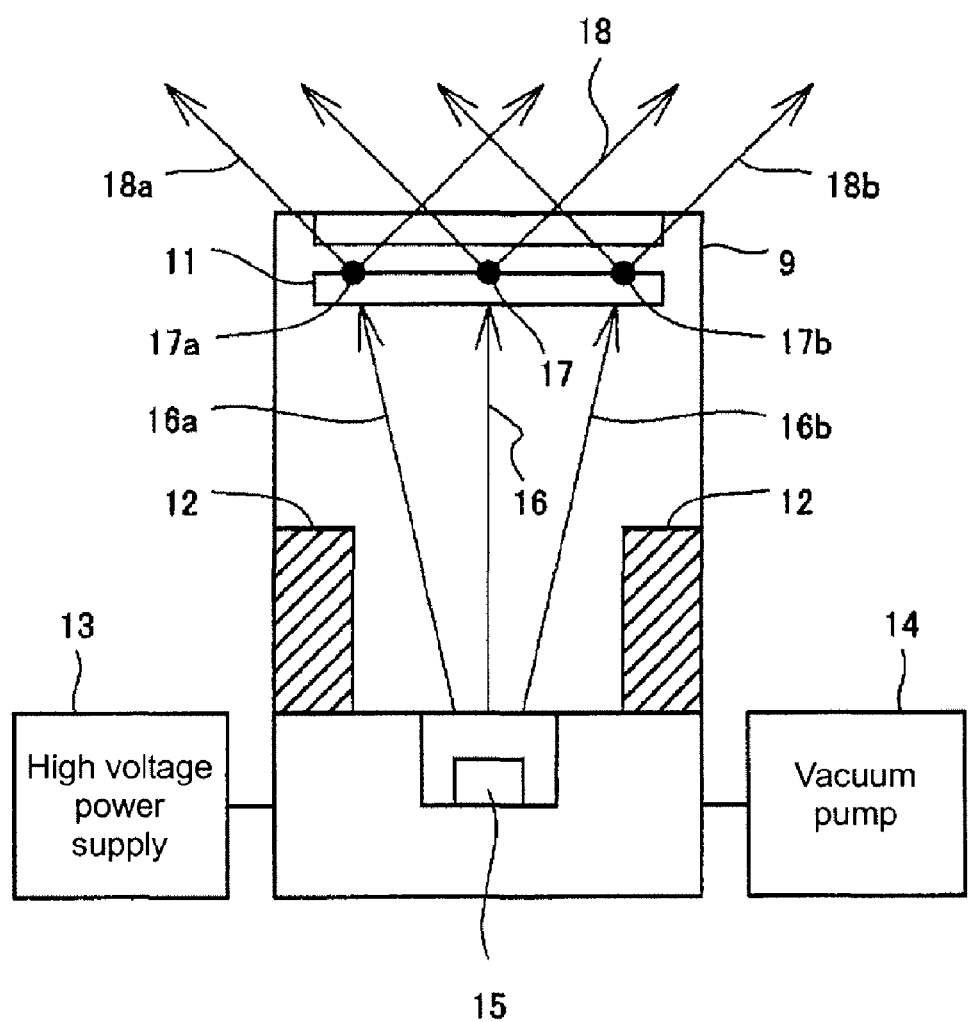
FIG. 2 shows a cross-sectional view showing a configuration of a scanning X-ray source 10.

FIG. 2 shows a cross-sectional view illustrating a configuration of the scanning X-ray source 10. With reference to FIG. 2, an electron beam 16 is applied to a target 11 such as tungsten from an electron gun 15 controlled by an electron beam controller 62 in the scanning X-ray source 10. An X-ray 18 is generated from a site (X-ray focal position 17) where the electron beam 16 impinges on the target and is emitted (outputted). An electron beam system is contained in a vacuum container 9. The inside of the vacuum container 9 is maintained in vacuum by a vacuum pump 14, and the electron beam 16 accelerated by a high voltage power supply 13 is emitted from the electron gun 15.

In the scanning X-ray source 10, the site where the electron beam 16 impinges on the target 11 can be appropriately changed by deflecting the electron beam 16 by means of a deflection yoke 12. For instance, an electron beam 16a deflected by the deflection yoke 12 impinges on the target 11, and an X-ray 18a is outputted from an X-ray focal position 17a. Similarly, an electron beam 16b deflected by the deflection yoke 12 impinges on the target 11, and an X-ray 18b is outputted from an X-ray focal position 17b. In the present invention, the scanning X-ray source 10 is a transmissive type, and a target having not a ring shape but a continuous surface is desirable so that, when generating the X-ray from a position (hereinafter referred to as a "starting position of an X-ray emission") to become the starting of the X-ray emission set according to the examination target portion of the examination target object, greater flexibility in setting the position can be provided, as will be described later. In the following description, the position is simply referred to as the X-ray focal position 17 as a collective term unless the position is particularly distinguished.

The position of the X-ray source itself can also be mechanically moved each time the X-ray focal position is moved to each of the above-mentioned starting positions of X-ray emission. However, with the configuration shown in FIG. 2, when moving the X-ray focal position to a starting position of X-ray emission, the X-ray source need not be mechanically moved if the movement distance is within a certain range, whereby an X-ray examination apparatus excelling in maintenance and reliability can be realized. A plurality of X-ray sources may be arranged so as to be switched at the time of use according to the starting positions.

Returning to FIG. 1, the scanning X-ray source control mechanism 60 includes an electron beam controller 62 for controlling the output of the electron beam. The electron beam controller 62 receives specification of the X-ray focal position and X-ray energy (tube voltage, tube current) from the calculation unit 70. The X-ray energy differs depending on the configuration of the examination target.

The examination target 20 is arranged between the scanning X-ray source 10 and the X-ray sensors 23 (sensor base 22). The examination target 20 may be moved to any position with an X-Y-Z stage, or may be arranged at a position for examination by moving the target in one direction like a belt conveyor. When the examination target is small as a printed mounting substrate, the examination target is moved with the scanning X-ray source 10 and the sensor base 22 fixed, but when the examination target is difficult to be arbitrarily moved since the examination target has a large area, such as a glass substrate, the scanning X-ray source 10 and the sensor base 22 are moved with the relative positions of the scanning X-ray source 10 and the sensor base 22 fixed.

The X-ray sensor 23 is a two-dimensional sensor for detecting and imaging an X-ray outputted from the scanning X-ray source 10 and transmitted through the examination target 20. The X-ray sensor 23 may be a CCD (Charge Coupled Device) camera, an I.I. (Image Intensifier) tube, or the like. In the present invention, an FPD (Flat Panel Detector) having satisfactory space efficiency is desirable since a plurality of X-ray sensors is arranged in the sensor base 22. High sensitivity is also desirable so that the sensor can be used in an in-line examination, and an FPD of direct conversion system using CdTe is particularly desirable. In the following description, the sensor is simply referred to as the X-ray sensor 23 as a collective term unless the sensor is particularly distinguished.

In the sensor base 22, the plurality of X-ray sensors 23 are attached on a circumference of the rotatable base on the scanning X-ray source 10 side. The sensor base 22 can rotate about the rotation axis 21 of the rotatable base. Actually, the rotatable range only needs to be less than or equal to one full rotation, and in the case where N pieces of X-ray sensors are arranged on the circumference of the sensor base 22, the angle formed by the adjacent X-ray sensors and the center of rotation of the sensor base only needs to rotate about 360/N. Obviously, this equation is merely one specific example, and the rotation angle is not limited by this equation. The rotation angle of the sensor base 22 is known by a sensor (not shown) and is retrieved into the calculation unit 70 via the input unit 40.

The sensor base 22 is desirably lifted and lowered in the vertical direction to adjust the magnification. In this case, the position of the sensor base 22 in the vertical direction is known by a sensor (not shown) and is retrieved into the calculation unit 70 via the input unit 40. When the sensor base 22 is lifted and lowered in the vertical direction, the angle of the X-ray entering the X-ray sensor 23 changes, and thus the inclination angle of the X-ray sensor 23 with respect to the sensor base 22 is desirably controllable.

The image acquiring control mechanism 30 includes a rotation angle controller 32 for performing control so that the sensor base is rotated at an angle specified by the calculation unit 70, and an image data acquiring part 34 for acquiring image data of the X-ray sensor 23 specified from the calculation unit 70. The X-ray sensor specified from the calculation unit 70 may be one or may be more than one.

The input unit 40 is an operation input device for accepting input of a user. The output unit 50 is a display for displaying X-ray image and the like configured in the calculation unit 70.

That is, the user can execute various input through the input unit 40, and various calculation results obtained by the processes of the calculation unit 70 are displayed on the output unit 50. The image displayed on the output unit 50 may be outputted for visible quality determination by the user or may be outputted as a quality determination result of a quality determination part 78 to be described later.

The calculation unit 70 includes a scanning X-ray source controller 72, an image acquiring controller 74, a 3D image reconstruction part 76, the quality determination part 78, a stage controller 80, an X-ray focal position calculating part 82, and an imaging condition setting part 84.

The scanning X-ray source controller 72 determines the X-ray focal position and the X-ray energy, and sends a command to the scanning X-ray source control mechanism 60.

The image acquiring controller 74 determines a rotation angle of the sensor base 22 and the X-ray sensor 23 to acquire the image and sends a command to the image acquiring control mechanism 30. The image data is acquired from the image acquiring control mechanism 30.

The 3D image reconstruction part 76 reconstructs three-dimensional data from a plurality of image data pieces acquired by the image acquiring controller 74.

The quality determination part 78 determines the quality of the examination target based on 3D image data reconstructed by the 3D image reconstruction part 76 or perspective data. For instance, quality determination can be made by recognizing the shape of a solder ball, and determining whether or not the shape is within a tolerable range defined in advance. An algorithm for making quality determination or input information to the algorithm are available from imaging condition information 94 as they differ depending on the examination target.

The stage controller 80 controls a mechanism (not shown) for moving the examination target 20. The X-ray focal position calculating part 82 calculates the X-ray focal position, an irradiation angle, and the like with respect to an examination area when examining a certain examination area of the examination target object 20. The details thereof will be described later.

The imaging condition setting part 84 sets conditions for outputting the X-ray from the scanning X-ray source 10 according to the examination target 20. The conditions include application voltage on the X-ray tube and imaging time.

The memory 90 includes X-ray focal position information 92 storing the X-ray focal position calculated by the X-ray focal position calculating part 82, and imaging condition information 94 storing imaging conditions set by the imaging condition setting part 84 and algorithms for performing quality determination. The memory 90 merely needs to be able to store data, and is configured by storage devices such as a RAM (Random Access Memory) and an EEPROM (Electrically Erasable and Programmable Read-Only Memory).

Figure 3B:
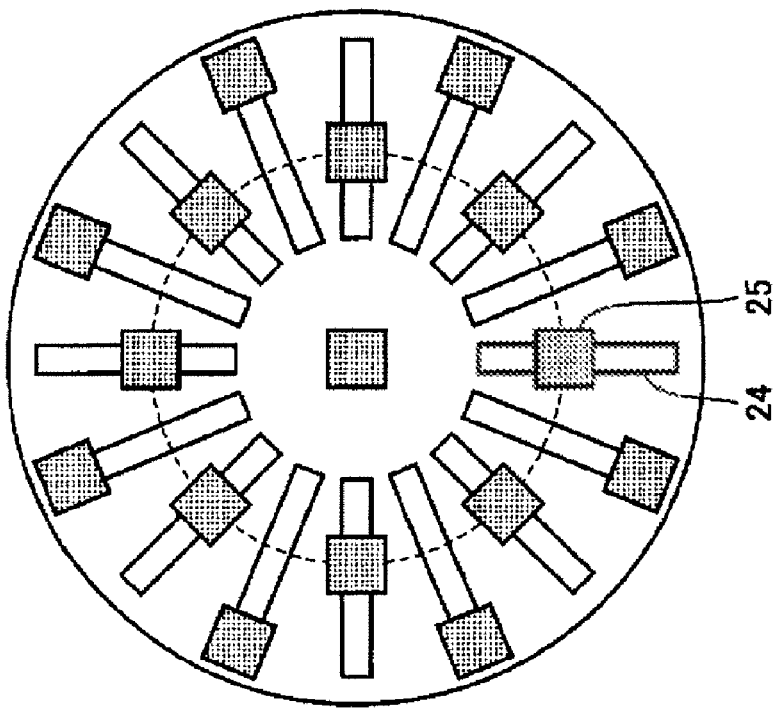
FIGS. 3A and 3B show views of a sensor base 22 when seen from the scanning X-ray source 10 side.
Figure 3A:
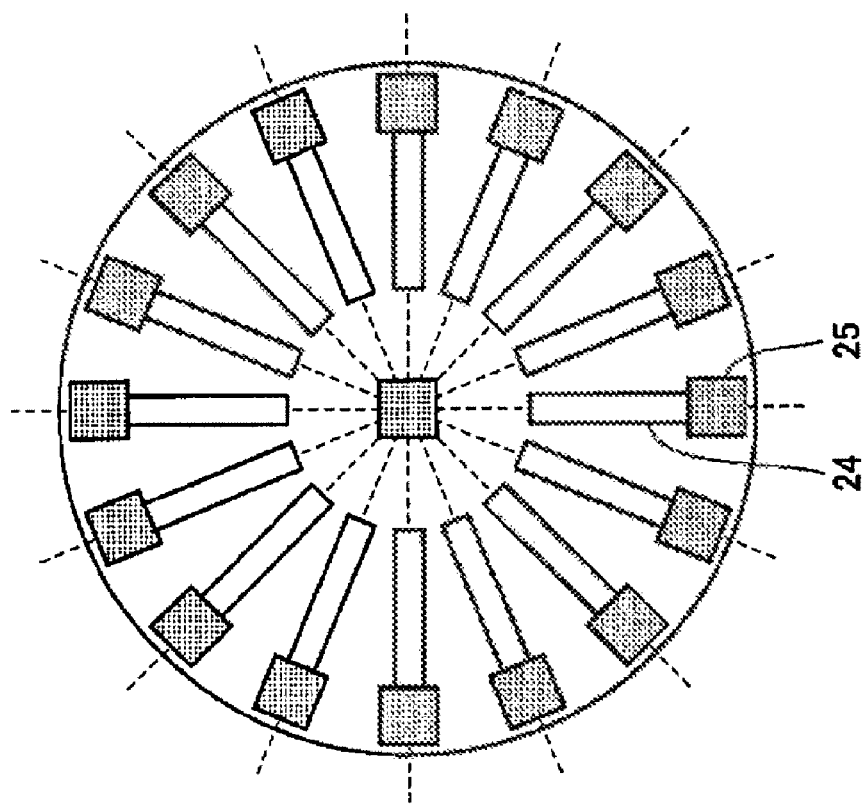

FIGS. 3A and 3B show views of the sensor base 22 when seen from the scanning X-ray source 10 side. In particular, FIG. 3A shows a view in which the X-ray sensors 23 arranged on the same radius, and FIG. 3B shows a view in which the X-ray sensors 23 are arranged on different radiuses.

The sensor base 22 will be described with reference to FIGS. 3A and 3B. A plurality of X-ray sensor modules 25 in which mechanism components for performing data processing and the like are compounded into the X-ray sensors 23 is attached to the sensor base 22. The X-ray sensor modules 25 may be arranged such that the X-ray sensor 23 is on the same radius of a circle having the center of rotation of the sensor base as a center, as shown in FIG. 3A, or may be arranged on circumferences of different radiuses, as shown in FIG. 3B. The sensor module 25 is desirably also arranged at the center of the sensor base 22. Further, the X-ray sensor modules 25 are desirably controlled so as to be freely movable in a radial direction by way of a slider 24. The imaged data of the examination target when seen from various angles thereby can be acquired.

Figure 4:
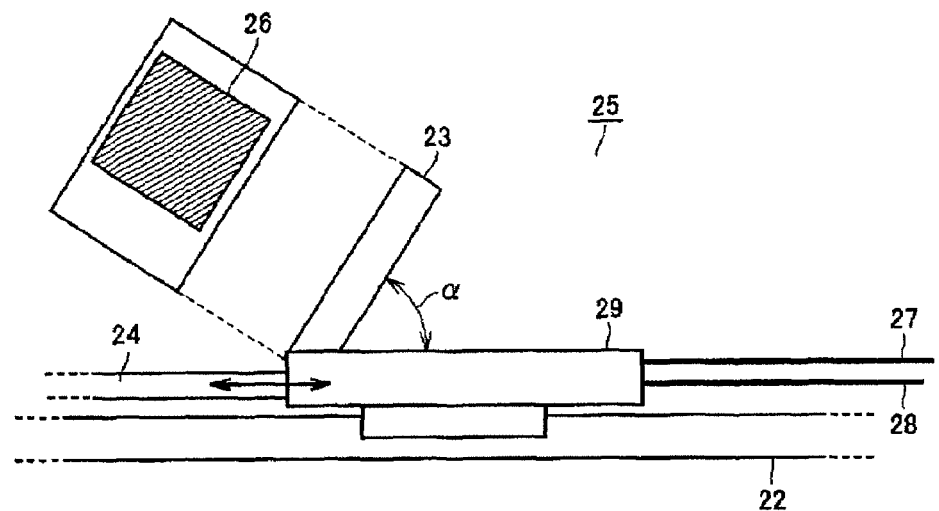
FIG. 4 shows a side view illustrating an X-ray sensor module 25.

FIG. 4 shows a side view illustrating the X-ray sensor module 25. A view of the X-ray sensor 23 when seen from an X-ray receiving part 26 side is also shown.

The X-ray sensor module 25 will be described with reference to FIG. 4. The X-ray sensor module 25 includes the X-ray receiving part 26 for converting the X-ray to an electric signal, and a data processing part 29 for creating data of the electric signal and transmitting the data to the image data acquiring part 34 through a data cable 27. Power is externally supplied to the X-ray sensor module 25 via a power supply cable 28. The X-ray sensor module 25 can be freely moved in a radial direction by way of the slider 24, but may be fixed at a position.

The X-ray sensor 23 is inclined at a certain angle (sensor inclination angle α) with respect to the sensor base 22. In FIG. 4, the sensor inclination angle α is fixed, but angular adjustment may be carried out by the control from the image acquiring control mechanism 30.

The plurality of X-ray sensor modules 25 are attached to the sensor base 22, but each of them is removable. Therefore, only the damaged X-ray sensor module can be replaced.

Figure 5:
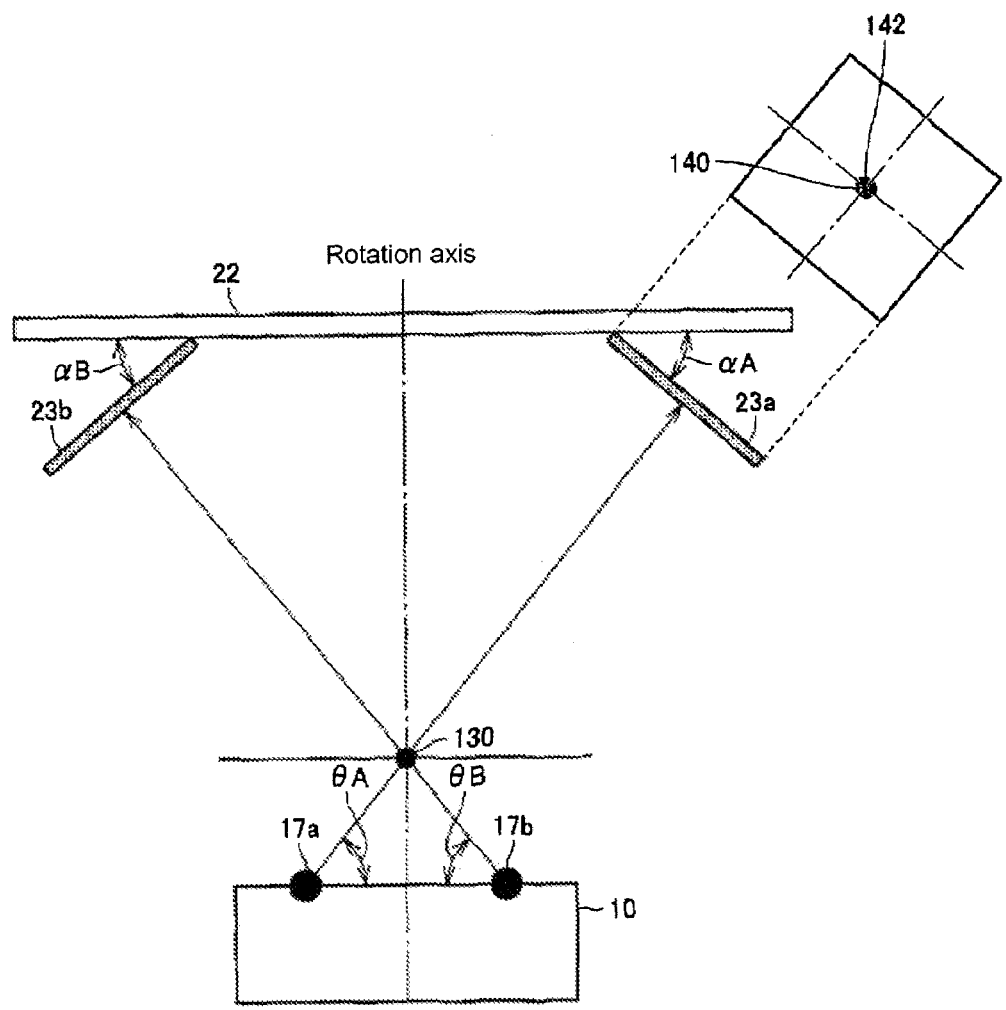
FIG. 5 shows a conceptual view of an imaging system seen from a side.

FIG. 5 shows a conceptual view of an imaging system seen from a side. The imaging system will be described with reference to FIG. 5. In FIG. 5, the X-ray sensors 23a and 23b may be any X-ray sensor 23 as long they are in an opposing position relationship. In FIG. 5, the X-ray sensors 23a and 23b are each inclined at a certain angle (sensor inclination angle αA, αB) with respect to the sensor base 22.

In FIG. 5, a workpiece (examination area) 130 is on the rotation axis of the sensor base 22. When imaging the workpiece 130, a position (starting position of X-ray emission) at which the focal position (irradiation position of electron beam) of the X-ray outputted from the scanning X-ray source 10 to the X-ray sensor 23 is to be set is determined. For instance, an X-ray focal position 17a with respect to the X-ray sensor 23a is set at an intersection of a straight line connecting the sensor center 140 of the X-ray sensor 23a with the center of the workpiece (examination area) 130 and the target surface of the scanning X-ray source 10. A perspective image 142 of the workpiece is detected at the sensor center 140. That is, the starting position of X-ray emission is set such that the X-ray transmits through the workpiece and enters the detection surface with respect to the detection surface of the corresponding X-ray sensor. Therefore, the sensor center 140 of the X-ray sensor 23a, the center of the workpiece 130, and the X-ray focal position 17a are desirably lined on the same straight line, but the arrangement is not limited to such an arrangement as long the X-ray enters within a certain range of the detection surface. In other words, the starting position of the target surface is set so that the workpiece exists on a straight line from each X-ray sensor to the corresponding starting position.

Suppose an angle formed by the straight line connecting the X-ray sensor 23 with the X-ray focal position 17 and the target surface of the scanning X-ray source 10 is an irradiation angle θ. For instance, the irradiation angles θA and θB are formed with respect to the X-ray sensors 23a and 23b, respectively. The angle is simply referred to as an irradiation angle θ unless each irradiation angle is particularly distinguished.

As shown in FIG. 5, when the workpiece exists on a perpendicular straight line of the center of rotation of the sensor base, the irradiation angles θ for all the X-ray sensors 23 become equal. In the present invention, the workpiece need not be on the center of rotation of the sensor base, and thus the irradiation angles are not always equal to each other.

Figure 6:
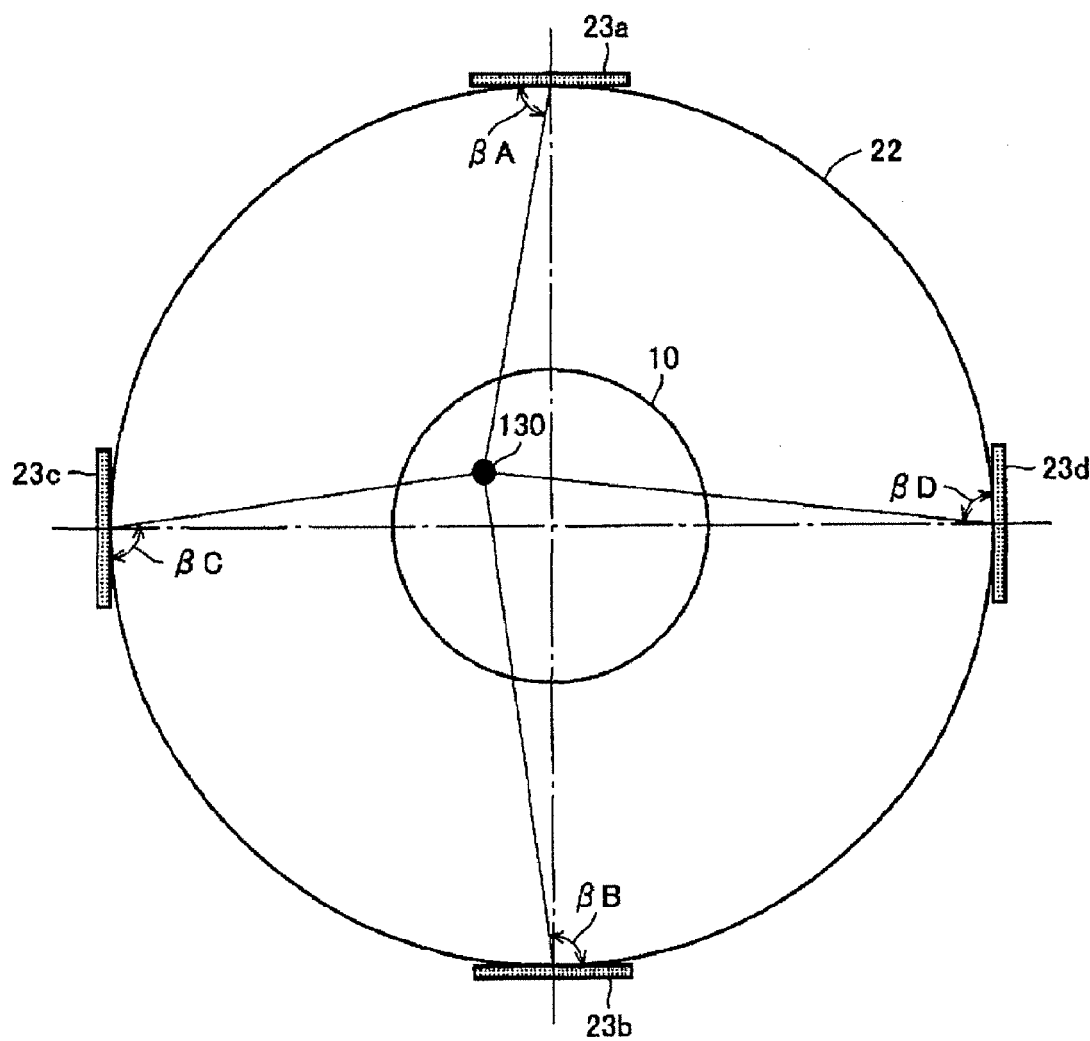
FIG. 6 shows a conceptual view of the imaging system seen from above.

FIG. 6 shows a conceptual view of the imaging system seen from above. The imaging system will be further described with reference to FIG. 6. As long as the positional relationship between the X-ray sensors 23a and 23b and the positional relationship between the X-ray sensors 23c and 23d are in a opposing relationship, these sensors may be any X-ray sensors 23. In FIG. 6, suppose that a straight line connecting the X-ray sensors 23a and 23b and a straight line connecting the X-ray sensors 23c and 23d are orthogonal.

Suppose an angle formed by a straight line connecting the center of the workpiece 130 with the center of the X-ray sensor 23 and the X-ray sensor is an imaging angle β. For instance, the imaging angles βA to βD are formed with respect to the X-ray sensors 23a to 23d. The angle is simply referred to as an imaging angle β unless each imaging angle is particularly distinguished.

When the workpiece 130 is on the perpendicular line of the center of the sensor base 22, the imaging angle is the same for all the X-ray sensors 23. However, when the workpiece 130 is not on the perpendicular line, the imaging angles are not the same, as shown in FIG. 6.

Figure 7:
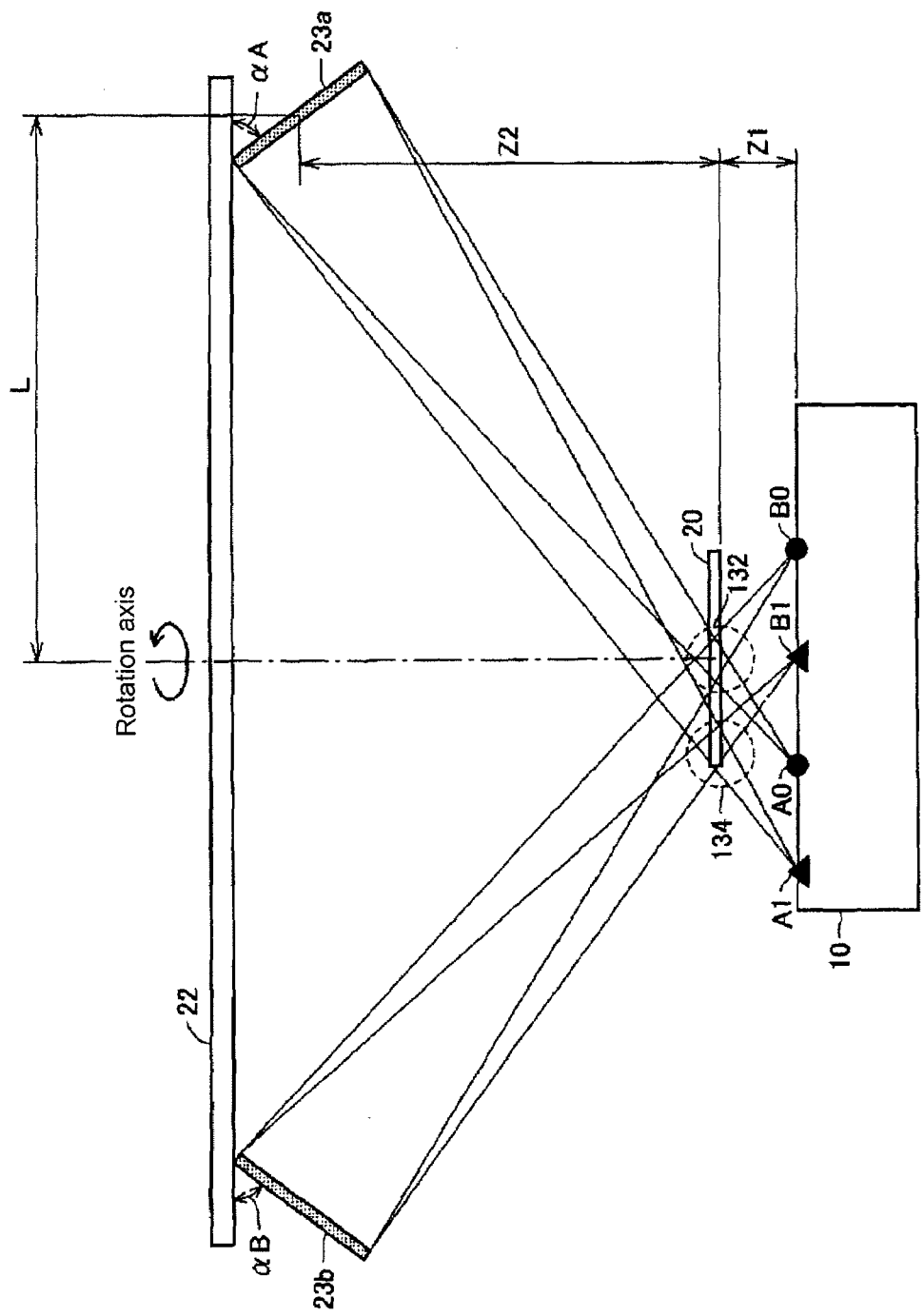
FIG. 7 shows a conceptual view of the imaging system seen from the side, illustrating an image when imaging examination areas having different positions in the lateral direction.

FIG. 7 shows a conceptual view of the imaging system seen from the side, illustrating an image when imaging examination areas having different positions in the lateral direction.

The X-ray focal position of when imaging the examination area having different positions in the lateral direction will be described with reference to FIG. 7 by way of an example. In FIG. 7, suppose a distance from the target surface of the scanning X-ray source 10 to the examination target 20 is Z1, a distance from the examination target 20 to a center of the X-ray sensor 23 is Z2, and a radius of the sensor base 22 (from the rotation axis of the sensor base 22 to the center of the X-ray sensor 23) is L.

When, e.g., it is desired to CT-image (reconstruct) an examination area 132 on the rotation axis of the sensor base 22, the X-ray focal position with respect to the X-ray sensor 23a is set to A0, and the X-ray focal position with respect to the X-ray sensor 23b is set to B0.

Similarly, in a case of an examination area 134 at a position that the examination area 132 is moved in the lateral direction, the X-ray focal position with respect to the X-ray sensor 23a is set to A1, and the X-ray focal position with respect to the X-ray sensor 23b is set to B1.

Figure 8:
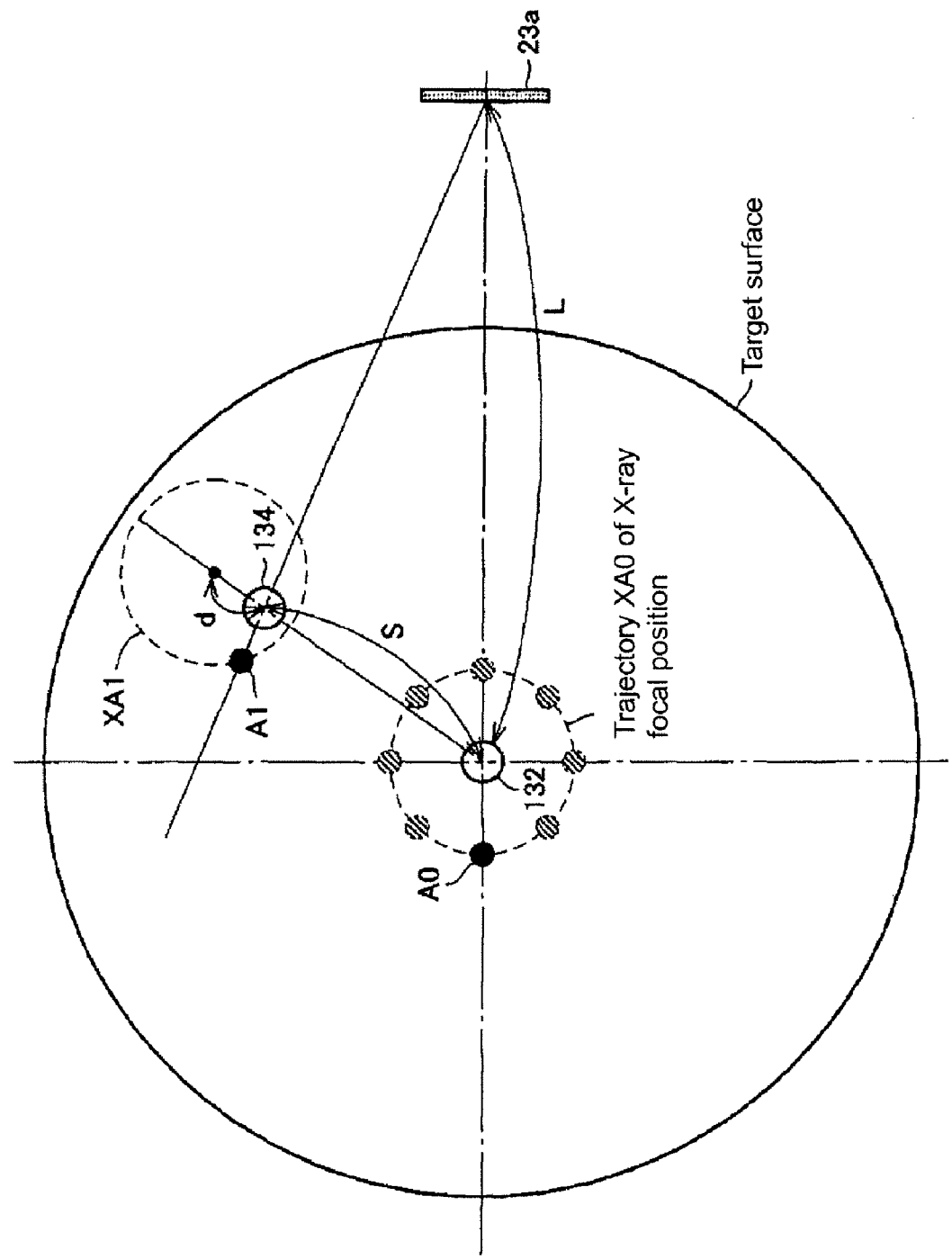
FIG. 8 shows a conceptual view of the imaging system when seen from above, illustrating an image of an X-ray focal position of the scanning X-ray source with respect to the examination area.

FIG. 8 shows a conceptual view of the imaging system when seen from above, illustrating an image of the X-ray focal position of the scanning X-ray source with respect to the examination area.

The X-ray focal position with respect to the examination area shown in FIG. 7 will be further described with reference to FIG. 8.

The X-ray focal position with respect to the X-ray sensor 23a for the examination area 132 on the rotation axis of the sensor base 22 is A0. The X-ray focal positions with respect to the X-ray sensors 23 for the examination area 132 form a circular trajectory (trajectory XA0 of X-ray focal position in FIG. 8) with the center at a point where the perpendicular straight line of the rotation center of the sensor base 22 and the target surface of the scanning X-ray source 10 intersect.

The X-ray focal position with respect to the X-ray sensor 23a for the examination area 134 at a position that the examination area 132 is moved within the same horizontal plane is A1. The X-ray focal position A1 is a point where the straight line connecting the center of the X-ray sensor 23a with the center of the examination area 134 and the target surface of the scanning X-ray source 10 intersect. A distance d between the center 135 of the trajectory XA1 of the X-ray focal position with respect to each X-ray sensor 23 for the examination area 134 and the examination area 134 is expressed as d=S/(Z2/Z1) using the distances Z1 and Z2 between the examination target 20 and the target surface and between the examination target 20 and the X-ray sensor described in FIG. 7. Note that S is the distance between the examination area 132 and the examination area 134.

Figure 9:
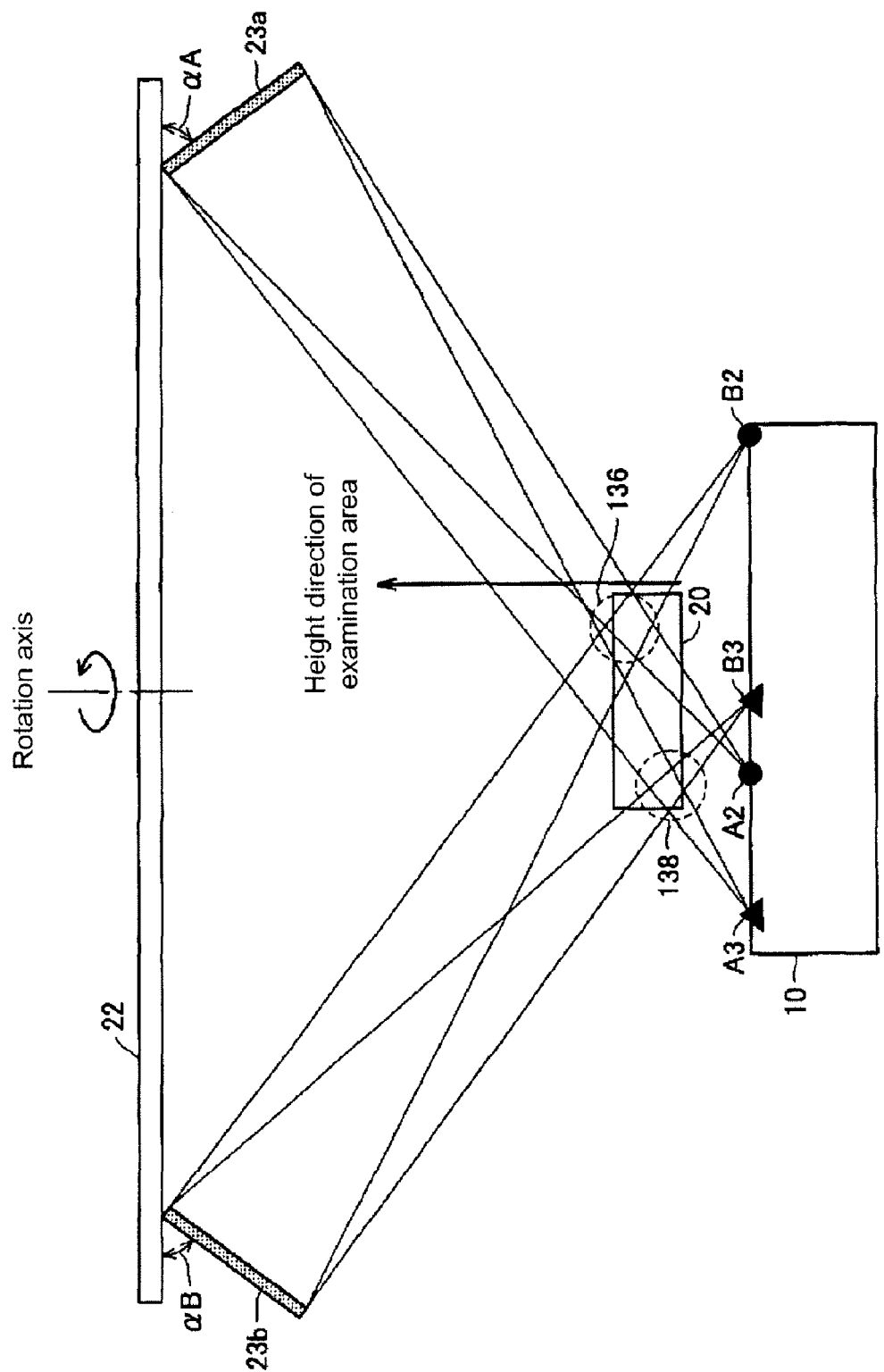
FIG. 9 shows a conceptual view of the imaging system seen from the side, illustrating an image when imaging examination areas having different positions in the lateral direction and the height direction.

FIG. 9 shows a conceptual view of the imaging system seen from the side, illustrating an image when imaging examination areas having different positions in the lateral direction and the height direction.

The X-ray focal position when imaging the examination areas having different positions in the lateral direction and the height direction will be described with reference to FIG. 9 by way of example.

The coordinates of examination areas 136 and 138 differ not only in the lateral direction but also in the height direction. The X-ray focal positions with respect to the X-ray sensors 23a and 23b for the examination area 136 are A2 and B2; and the X-ray focal positions with respect to the X-ray sensors 23a and 23b for the examination area 138 is A3 and B3.

The magnification in the projection to the X-ray sensor is inversely proportional to the height from the target surface to the center of the examination area. Thus, the examination areas 136 and 138 having different heights from the target surface to the center of the examination area differ in magnification when projected to the X-ray sensor 23. However, even if the sizes of the reconstructed images differ, examination is not impeded, and correction in magnification merely needs to be performed on the reconstructed images in the image processing when comparing or combining the examination areas.

Figures 10A, 10B:
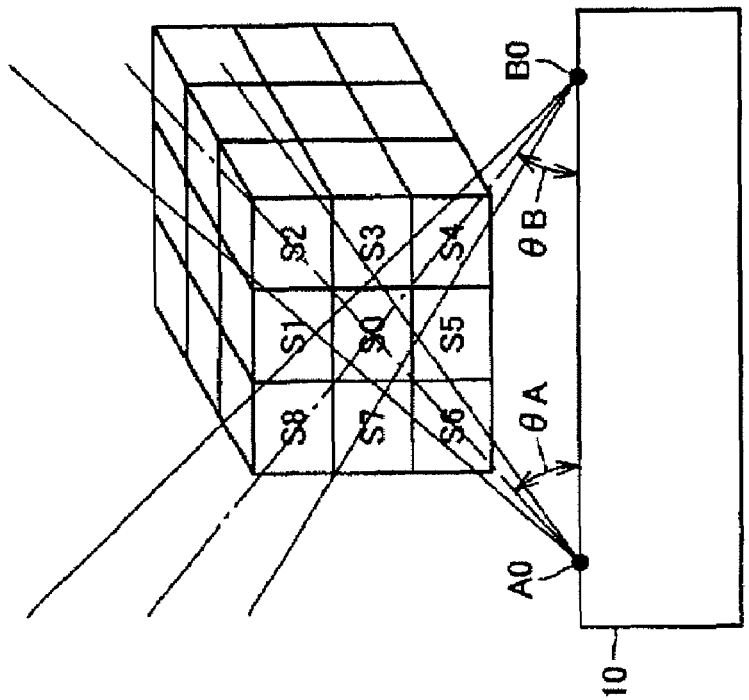
FIGS. 10A and 10B show diagrams showing a correspondence relationship between the examination area and X-ray focal position information.

FIGS. 10A and 10B show diagrams illustrating a correspondence relationship between the examination area and X-ray focal position information. In particular, FIG. 10A shows a diagram illustrating an examination area within a reconstruction region which is a target of reconstruction, and FIG. 10B shows a diagram illustrating the X-ray focal position information including information necessary for reconstruction by a CT algorithm with respect to each examination area. The CT algorithm will be described later.

The examination area and the X-ray focal position information will be described with reference to FIGS. 10A and 10B. As shown in FIG. 10A, the reconstruction region can be divided into regions of voxels such as examination areas S0, . . . , S8, . . . . A table showing the information necessary for reconstruction of images with respect to each examination area is the X-ray focal position information shown in FIG. 10B.

In the X-ray focal position information, an examination area 200, a sensor name 202 indicating the name assigned to each X-ray sensor 23, a sensor inclination angle 204, a sensor imaging angle 206, a focal position 208, an irradiation angle 210, and a sensor arrangement angle 212 are associated with one another. Information necessary for reconstruction in a case where the sensor base is rotated is also associated with respect to each examination area. The sensor arrangement angle will be described later.

The X-ray focal position indicates the irradiation position of the electron beam with respect to each X-ray sensor when imaging a certain examination area, and the sensor inclination angle, the sensor imaging angle, the irradiation angle, and the sensor arrangement angle are used in calculation for reconstructing an image from the imaged data. The angles may be calculated in advance, or may be calculated every time the X-ray is emitted onto the X-ray sensor.

For instance, when imaging an examination area S0 when the sensor base is not rotating, the electron beam is deflected, and the position of irradiation of the electron beam is moved to the X-ray focal position A0 in the scanning X-ray source. The imaged data of the corresponding X-ray sensor A is then acquired. Similarly, the irradiation position is moved to the X-ray focal position B0, and the imaged data of the corresponding X-ray sensor B is acquired. This is repeated for the number of X-ray sensors. Imaging is performed with the irradiation position of the electron beam moved according to the rotation angle of the sensor base in a case where the sensor base is rotated to increase the number of imaging.

Figure 11B:
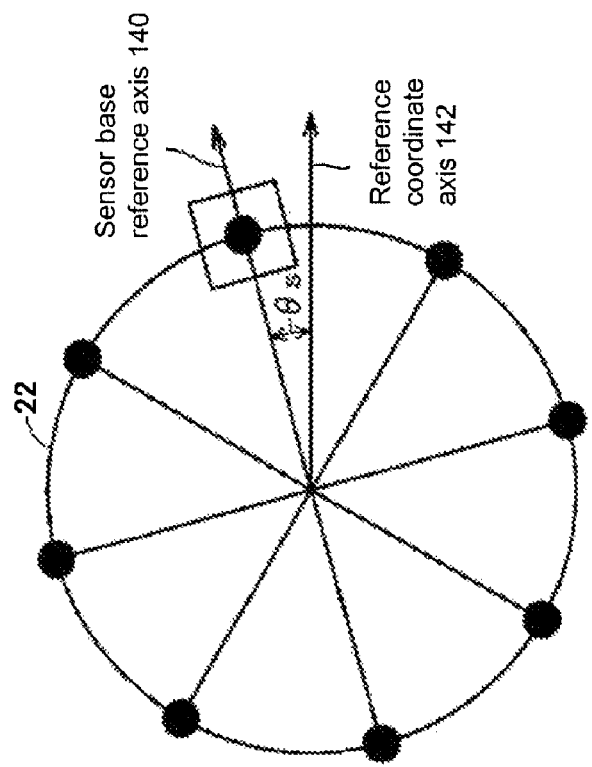
FIGS. 11A and 11B show diagrams illustrating a sensor arrangement angle and a sensor base reference angle.
Figure 11A:
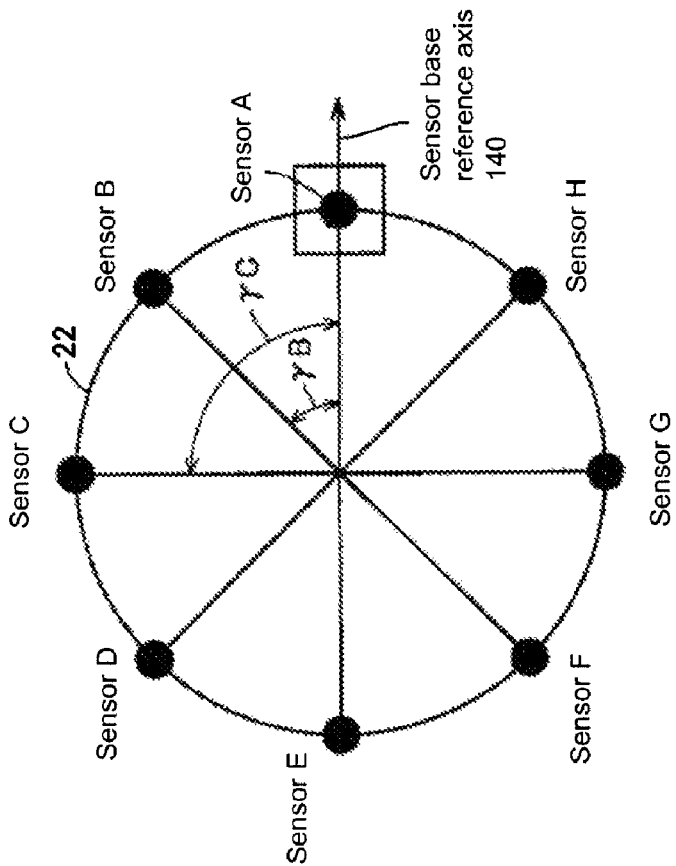

FIGS. 11A and 11B shows diagrams illustrating the sensor arrangement angle and a sensor base reference angle. In particular, FIG. 11A shows a diagram of the sensor base before being rotated, and FIG. 11B shows a diagram of the sensor base after being rotated by θs.

The sensor arrangement angle and the sensor base reference angle will be described with reference to FIGS. 11A and 11B. As shown in FIG. 11A, a sensor base reference axis 140 that serves as a reference when indicating the positional relationship between the X-ray sensors 23 is defined in the sensor base 22.

Suppose an angle formed by the X-ray sensor 23 and the sensor base reference axis 140 is the sensor arrangement angle γ. For instance, the sensor arrangement angles γB and γC are formed with respect to the X-ray sensors B and C, respectively. The angle is simply referred to as a sensor arrangement angle γ unless each sensor arrangement angle is particularly specified.

As shown in FIG. 11B, suppose an angle formed by a reference coordinate axis 142 and the sensor base reference axis 140 in the sensor base 22 is the sensor base reference angle θs.

The X-ray examination process described in the next section is then performed using the X-ray examination apparatus 100 having the above configuration.

(2. Flow of the X-Ray Examination Process)

Figure 12:
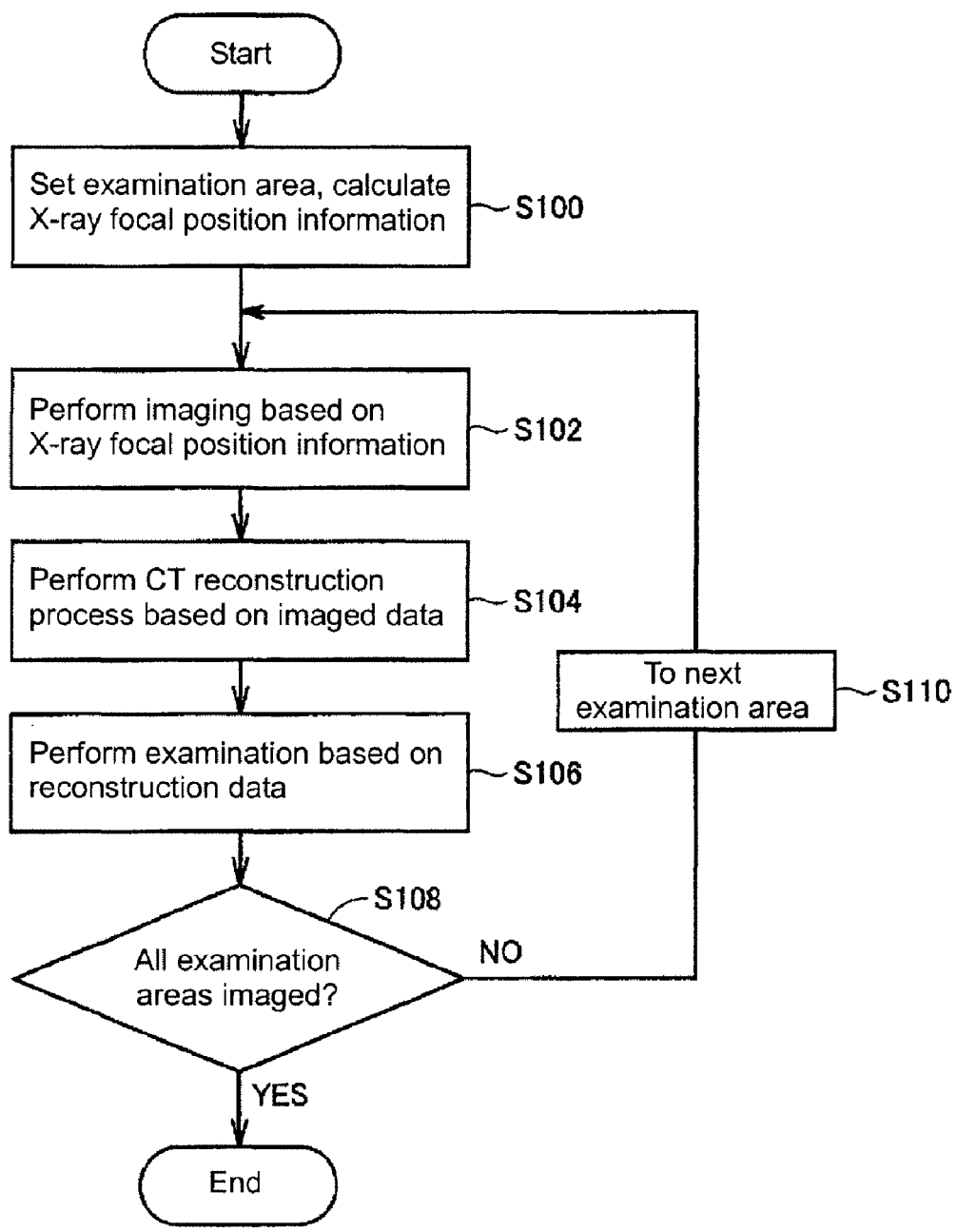
FIG. 12 shows a flowchart illustrating an outline of an X-ray examination process of the X-ray examination apparatus 100.

FIG. 12 shows a flowchart illustrating an outline of the X-ray examination process of the X-ray examination apparatus 100.

The outline of the X-ray examination process will be described with reference to FIG. 12. The details of steps S100 to S104 will be described later. This flowchart is merely an example of the X-ray examination process, and may be executed with the steps interchanged.

First, in step S100, an examination area is set, and the X-ray focal position information is calculated. The examination area may be set by the user as appropriate through the input unit 40, or may be set referencing the information of the examination area set in advance. A plurality of examination areas may also be set. The calculation unit 70 calculates the X-ray focal position information.

Next, in step S102, imaging is carried out based on the X-ray focal position information. In this step, the process may proceed to the process of step S104 after all the imaging processes are completed with respect to each X-ray sensor 23, or steps S102 and S104 may be performed in parallel in which case the imaged image data is sequentially provided for the process of step S104.

Subsequently, in step S104, back projection is performed from the plurality of imaged data to a three-dimensional reconstruction space to generate reconstruction data and obtain a CT image according to the CT algorithm.

In step S106, examination is carried out based on the reconstruction data. The examination includes a case where the user performs the examination with the reconstruction data displayed on a display or the like, and a case where decision is automatically made from the reconstruction data.

Lastly, in step S108, the calculation unit 70 determines whether or not imaging of all the examination areas set in step S100 is finished. If determined that the imaging of all the examination areas is not finished (NO in step S108), the examination area to be imaged is changed to a next set examination area in step S110, and the process returns to the process of step S102.

If determined that the imaging of all the examination areas is finished (YES in step S108), the X-ray examination process is finished.

Figure 13:
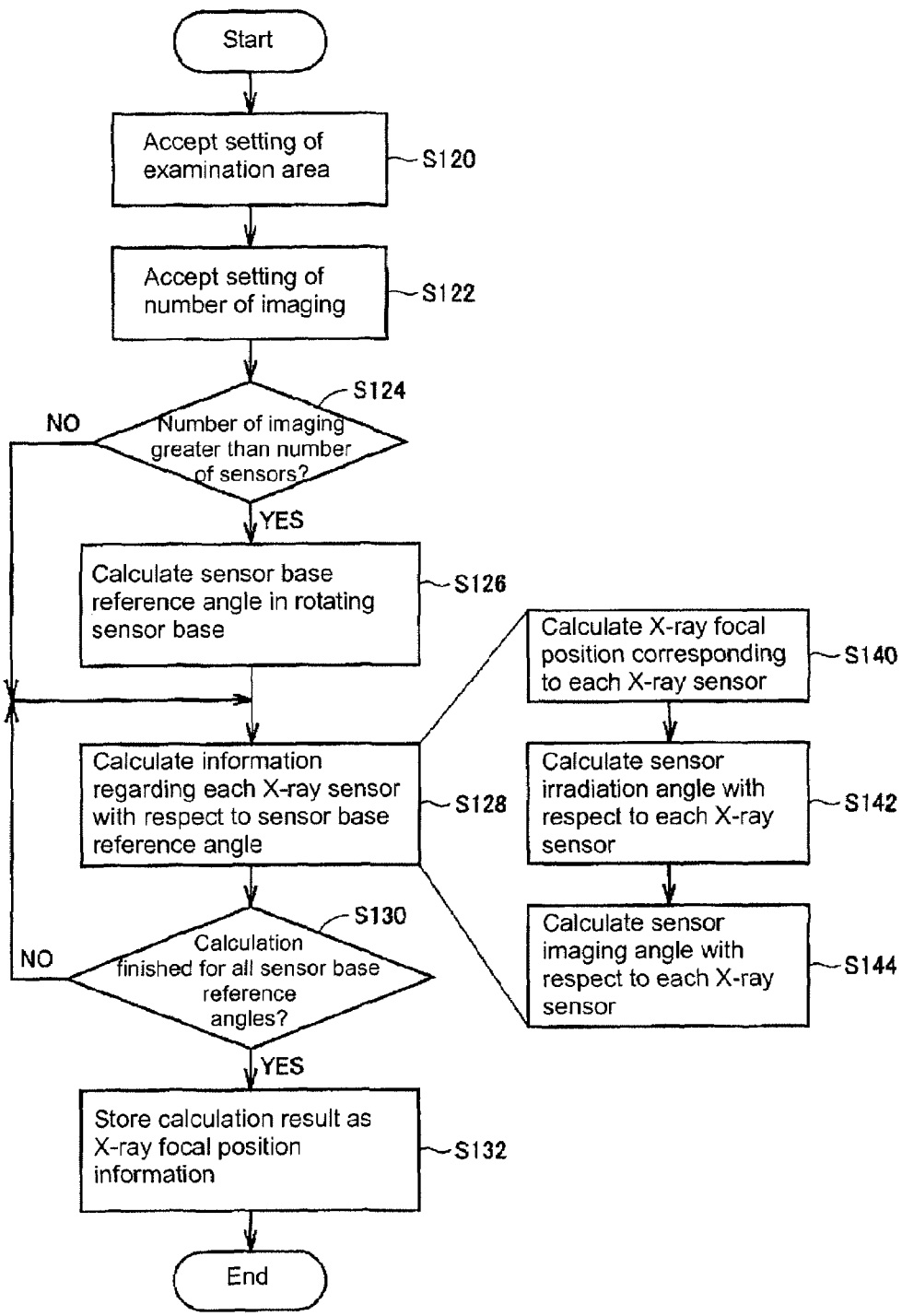
FIG. 13 shows a flowchart illustrating the process in step S100 of FIG. 12.

FIG. 13 shows a flowchart illustrating the process in step S100 of FIG. 12.

The details of the process in step S100 of FIG. 12 will be described with reference to FIG. 13. In step S120, the input unit 40 accepts the setting of the examination area by the user. The location (e.g., position coordinates) of the examination area is then provided to the X-ray focal position calculating part 82.

Next, in step S122, the input unit 40 accepts the setting of the number of imaging by the user. The number of imaging is then provided to the X-ray focal position calculating part 82. The number of imaging may be automatically set by the imaging condition setting part 84 according to the examination target and the examining item, or may be appropriately set by the user. In the present embodiment, the number of imaging is an integral multiple of the number of X-ray sensors attached to the sensor base on the circumference.

Subsequently, in step S124, the X-ray focal position calculating part 82 determines whether or not the set number of imaging is greater than the number of the X-ray sensors attached to the sensor base on the circumference.

If determined that the number of imaging is greater than the number of the X-ray sensors (YES in step S124), the X-ray focal position calculating part 82 calculates the sensor base reference angle in rotating the sensor base, in step S126.

If there are n pieces of X-ray sensors 23, and the number of imaging is n×m (m is an integer greater than or equal to 2), m pieces of sensor base reference angles are calculated. Specifically, the sensor base angles are 0 degree, 360/n/m degrees, . . . , (360/n/m)×x degrees (x=1, . . . , m−1).

For instance, an example of n=18 and m=10 will be described by way of example. In this case, the number of imaging is 18×10=180. The second sensor base reference angle is 360/18/10=2 degrees, and the last sensor base reference angle is (360/18/10)×9=18 degrees.

If determined that the number of image is less than the number of the X-ray sensors (NO in step S124), the process proceeds to step S128.

In step S128, the X-ray focal position calculating part 82 calculates the information on each X-ray sensor with respect to the sensor base reference angle. Specifically, the following calculation is performed.

In step S140, the X-ray focal position calculating part 82 calculates the X-ray focal position corresponding to each X-ray sensor. For instance, the intersection of the straight line connecting the center of the X-ray sensor with the center of the examination area and the target surface is set as the X-ray focal position.

In step S142, the X-ray focal position calculating part 82 calculates the sensor irradiation angle based on the X-ray focal position.

In step S144, the X-ray focal position calculating part 82 calculates the sensor imaging angle based on the X-ray focal position.

The X-ray focal position information is calculated in the above manner. In the present embodiment, the sensor inclination angle α and the sensor arrangement angle γ need not be recalculated for every X-ray focal position, as they are set in advance.

Subsequently, in step S130, the X-ray focal position calculating part 82 determines whether calculation is finished on all the sensor base reference angles.

If determined that the calculation is not finished on all the sensor base reference angles (NO in step S130), the process returns to the process of step S128.

Meanwhile, if determined that the calculation is finished on all the sensor base reference angles (YES in step S130), the X-ray focal position calculating part 82 stores and retains the calculation result regarding the focal position in the X-ray focal position information 92.

The X-ray focal position calculating part 82 performs the process of calculating the X-ray focal position information in the above manner.

Figure 14:
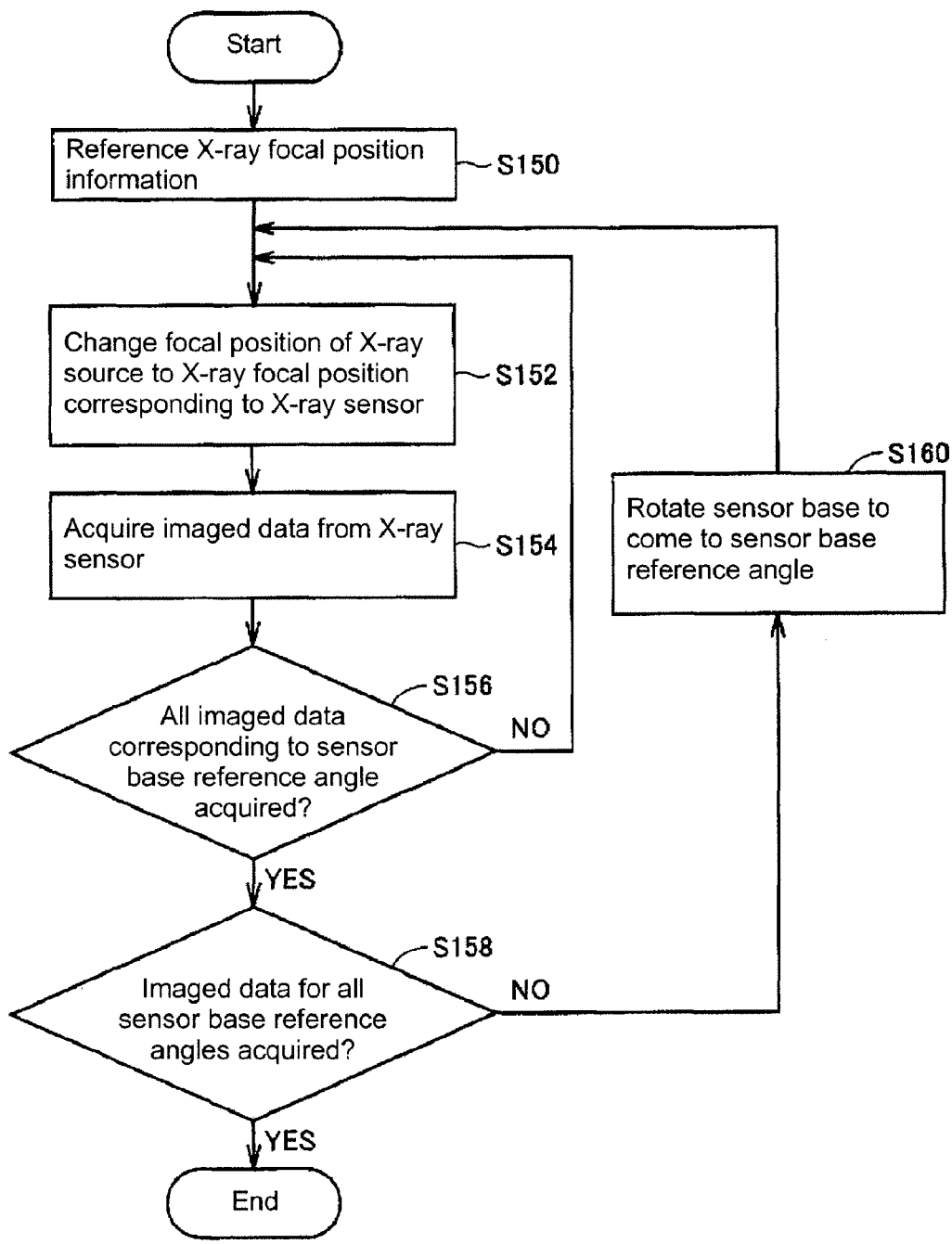
FIG. 14 shows a flowchart illustrating the process in step S102 of FIG. 12.

FIG. 14 shows a flowchart illustrating the process in step S102 of FIG. 12.

The details of the process in step S102 of FIG. 12 will be described with reference to FIG. 14. First, the scanning X-ray source controller 72 references the X-ray focal position information 92 in step S150.

Then, in step S152, the scanning X-ray source controller 72 instructs the scanning X-ray source 10 to perform control on the electron beam controller 62 to change the irradiation position of the electron beam to the X-ray focal position corresponding to the X-ray sensor.

Subsequently, in step S154, the image acquiring controller 74 instructs the image data acquiring part 34 to acquire imaged data from the X-ray sensor that detected the X-ray transmitted through the examination area.

In step S156, the image acquiring controller 74 determines whether or not all the pieces of imaged data corresponding to the sensor base reference angle are acquired.

If determined that all the pieces of imaged data are not acquired (NO in step S156), the process returns to the process of step S152.

If determined that all the pieces of imaged data are acquired (YES in step S156), the image acquiring controller 76 determines whether or not the imaged data with respect to all the sensor base reference angles are acquired in step S158.

If determined that the imaged data is not acquired for all the sensor base reference angles (NO in step S158), the image acquiring controller 74 instructs the rotation angle controller 32 to perform control to rotate the sensor base 22 so as to come to the sensor base reference angle which has not yet been rotated to in step S160, and the process proceeds to the process of step S152.

On the other hand, if determined that the imaged data is acquired for all the sensor base reference angles (YES in step S158), the imaging process is terminated.

Figure 15:
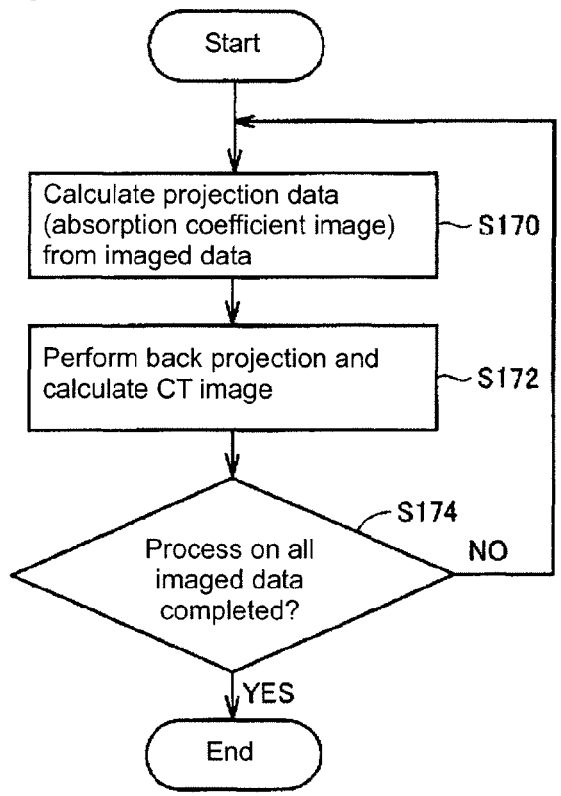
FIG. 15 shows a flowchart illustrating the process in step S104 of FIG. 12.

FIG. 15 shows a flowchart illustrating the process in step S104 of FIG. 12.

The details of the process (CT algorithm) in step S104 of FIG. 12 will be described with reference to FIG. 15.

In step S170, the 3D image reconstruction part 76 calculates projection data (absorption coefficient image) from the acquired imaged data.

The projection data will be briefly described. Generally, when the X-ray transmits through the examination target object, the X-ray quantity attenuates as expressed with the exponential function of the following equation (1) by the amount corresponding to the unique X-ray absorption coefficient of each component configuring the examination target object and the like.

$$I = I_0 \mathrm{Exp}(-\mu L) \tag{1}$$

where L is a transmission path length, $\mu$ is an X-ray absorption coefficient, $I_0$ is an X-ray air data value, and I is X-ray sensor imaged data. The X-ray air data value is imaged data of the X-ray sensor imaged without arranging the examination target object and is generally referred to as a white image.

The projection data ($\mu L$) calculated with the following equation (2) is obtained from equation (1).

$$\mu L = \log(I_0/I) \tag{2}$$

Various corrections are sometimes made on the projection data or the X-ray imaged data before the calculation of the projection data. For instance, a median filter may be applied to remove noise, or calibration may be performed if characteristics and/or sensitivity differ per pixel in the X-ray sensor.

In step S172, the 3D image reconstruction part 76 performs reconstruction of image data from a plurality of projection data calculated in step S170. Various methods such as Fourier transform are proposed for the reconstruction method as described in "Digital image processing" (edited by Digital image processing editorial board, published by Computer Graphic Arts Society (CG-ARTS), second edition, published March 2006), pp. 149-154. In the present embodiment, convolution back projection method is used for the reconstruction method. This is a method of back projection by convoluting a filter function such as Shepp-Logan to the projection data to reduce blurs.

Figure 16:
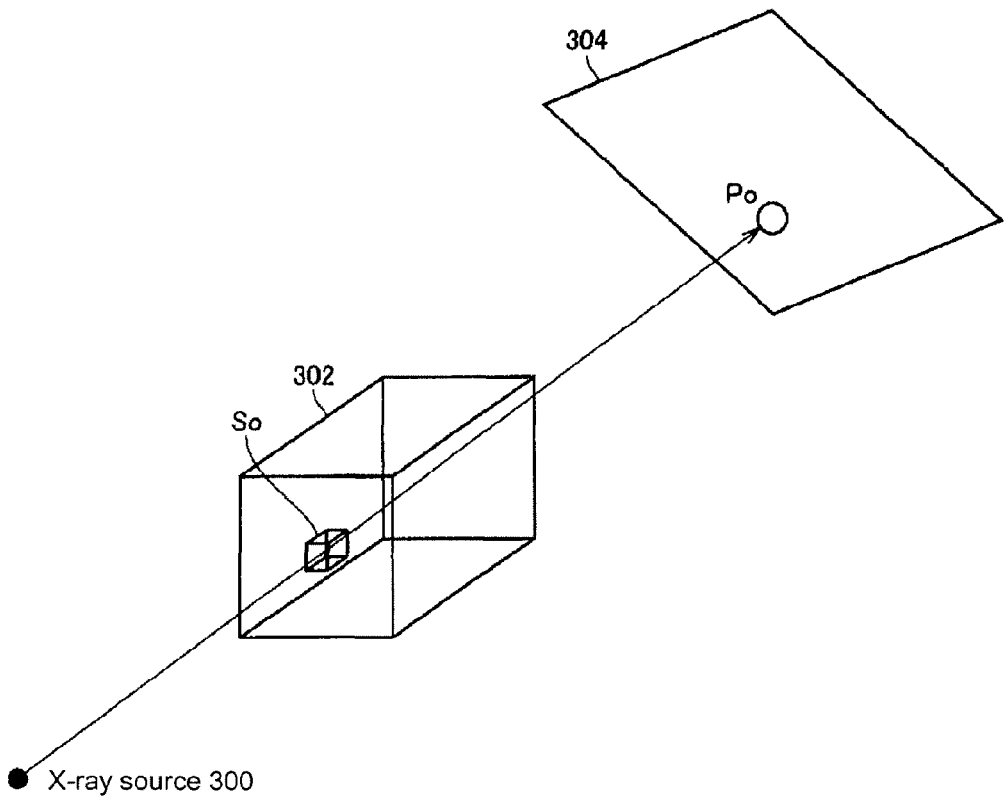
FIG. 16 shows a diagram illustrating back projection.

Back projection will be briefly described. FIG. 16 shows a diagram illustrating back projection.

A case of back projecting voxel data $S_0$ of the reconstruction region 302 will be described by way of example.

In this case, a value of the projection data of a point (pixel of X-ray sensor 304) $P_0$ where the straight line connecting an X-ray source 300 with the voxel data $S_0$ and an X-ray sensor 304 intersect is set as a value of the voxel data $S_0$. Since the X-ray intensity differs depending on the position (coordinates) of the voxel in this case, intensity correction such as FDK method may be made on the imaged data based on the sensor inclination angle, the sensor imaging angle, the irradiation angle, the sensor arrangement angle, and the sensor base reference angle. A pixel $P_0$ can be geometrically calculated from the information stored in the X-ray focal position information 92, and the values of the distance Z1 from the target surface to the examination target and of the distance Z2 from the examination target to the center of the X-ray sensor.

Returning to FIG. 15, the 3D image reconstruction part 76 lastly determines whether or not the process on all the imaged data is completed in step S174.

If determined that the process on all the imaged data is not completed (NO in step S174), the process returns to the process of step S170.

If determined that the process on all the imaged data is completed (YES in step S174), the process is terminated.

As described above, according to the X-ray examination apparatus of the present invention, any examination area can be set for the examination target object, and the image can be reconstructed only with respect to such a limited area. Thus, time is not required for imaging/reconstruction, and the examination time can be reduced.

According to the X-ray examination apparatus according to the present invention, the examination area can be changed without moving the examination target object. Thus, the apparatus excels in terms of cost, maintenance, and reliability since the operating part can be reduced. The reconstruction calculation can be performed even in a case where the examination target object is difficult to be moved.

According to the X-ray examination apparatus of the present invention, the examination area can be imaged while rotating the sensor base. Thus, the number of imaging can be increased, and a high precision image can be reconstructed.

The embodiment disclosed herein is merely illustrative in all aspects, and should not be construed as being limitative. The scope of the present invention is defined by the claims and not by the description given above, and the meaning equivalent to the claims and all modifications within the scope of the claims are intended to be encompassed.

What is claimed is:

1. An X-ray examination method using an X-ray examination apparatus including a light receiving part for detecting an X-ray transmitted through an object by X-ray irradiation with a plurality of X-ray sensors, the method comprising the steps of:

specifying an examining portion of the object;

generating the X-ray by moving, with respect to the plurality of X-ray sensors, an X-ray focal position of an X-ray source to each starting position of X-ray emission set such that the X-ray transmits through the examining portion and enters each of the X-ray sensors;

detecting an intensity distribution of the X-ray transmitted through the examining portion at each of the X-ray sensors; and reconstructing image data of the examining portion based on data of the detected intensity distribution, wherein the step of generating the X-ray includes:

specifying a plurality of X-ray sensors for detecting the X-ray;

setting each starting position on a target surface which is a continuous surface of the X-ray source such that the examining portion is on a straight line from each of the plurality of X-ray sensors to the starting position; and generating the X-ray by changing an irradiation position to apply an electron beam of the X-ray source to each starting position and moving the X-ray focal position, wherein the step of detecting an intensity distribution includes:

arranging a rotatable base with the plurality of X-ray sensors on a circumference having a predetermined axis as a center; and rotating the rotatable base about the axis, wherein the X-ray source is a scanning X-ray source.

2. The X-ray examination method according to claim 1, wherein the step of setting each starting position includes the step of determining an intersection of a straight line connecting the X-ray sensor and the examining portion and the target surface as the starting position.

3. The X-ray examination method according to claim 1, wherein the step of generating the X-ray includes the step of changing the irradiation position by deflecting the electron beam.

4. An X-ray examination apparatus including a light receiving part for detecting an X-ray transmitted through an object by X-ray irradiation with a plurality of X-ray sensors, the X-ray examination apparatus comprising:

a detection unit including the plurality of X-ray sensors; and an output controller for controlling an output process of the X-ray, wherein the output controller includes:

a specifying part for specifying an examining portion of the object;

a starting point setting part for setting, with respect to the plurality of X-ray sensors, each starting position of X-ray emission such that the X-ray transmits through the examining portion of the object and enters each of the X-ray sensors;

an X-ray output part for moving an X-ray focal position of an X-ray source to each starting position and generating the X-ray; and a reconstruction part for reconstructing image data of the examining portion based on data of an intensity distribution of the X-ray transmitted through the examining portion detected at the plurality of X-ray sensors, wherein the detection unit includes:

a rotatable base arranged with the plurality of X-ray sensors on a circumference having a predetermined axis as a center; and a rotating part for rotating the rotatable base about the axis, wherein the X-ray source is a scanning X-ray source.

5. The X-ray examination apparatus according to claim 4, wherein the X-ray output part includes a part for deflecting an electron beam of the X-ray source and changing an irradiation position of applying the electron beam to move the X-ray focal position.

6. The X-ray examination apparatus according to claim 4, wherein the plurality of X-ray sensors are arranged on a circumference having an axis perpendicular to the object as a center.

7. The X-ray examination apparatus according to claim 6 wherein the detection unit includes a part for freely moving each X-ray sensor in a radial direction of a circle having the perpendicular axis as the center.

8. The X-ray examination apparatus according to claim 4, wherein the plurality of X-ray sensors are arranged on a plurality of circumferences having different radiuses with an axis perpendicular to the object as a center.

9. The X-ray examination apparatus according to claim 4, wherein the detection unit includes a detection surface controller for controlling an inclination angle formed by an axis perpendicular to the object and each of each X-ray sensor.

* * * * *